(12) United States Patent
Chung et al.

(10) Patent No.: US 6,444,144 B1
(45) Date of Patent: Sep. 3, 2002

(54) POLYETHOXYLATED ASCORBIC ACID DERIVATIVES AS A NOVEL ANTIOXIDANT AND PROCESS FOR PREPARING THEREOF

(75) Inventors: Bong Youl Chung; In Sang Lee; Bong Jun Park; Young Keun Kim; Wan Goo Cho; Young Sook Song, all of Taejeon (KR)

(73) Assignee: LG Chemical Ltd., Seoul (KR)

( * ) Notice: Subject to any disclaimer, the term of this patent is extended or adjusted under 35 U.S.C. 154(b) by 0 days.

(21) Appl. No.: 09/671,094

(22) Filed: Sep. 27, 2000

Related U.S. Application Data

(63) Continuation of application No. PCT/KR99/00148, filed on Mar. 27, 1999.

(30) Foreign Application Priority Data

Mar. 27, 1998 (KR) ............................................ 98-10752
Mar. 16, 1999 (KR) ............................................ 98-8784

(51) Int. Cl.⁷ ................................................ C09K 15/06
(52) U.S. Cl. ........................................ 252/407; 549/315
(58) Field of Search ........................... 549/315; 252/407

(56) References Cited

U.S. PATENT DOCUMENTS

| | | | | |
|---|---|---|---|---|
| 4,959,362 A | * | 9/1990 | Terao et al. | 514/231.5 |
| 5,008,405 A | * | 4/1991 | Hatanaka et al. | 549/315 |
| 5,034,543 A | * | 7/1991 | Satoh et al. | 549/315 |
| 5,587,149 A | * | 12/1996 | Punto | 424/59 |

FOREIGN PATENT DOCUMENTS

| | | | |
|---|---|---|---|
| EP | 146121 | * | 6/1985 |
| JP | 5857373 | * | 8/1983 |
| JP | 58131978 | * | 1/1984 |
| JP | 02237983 | * | 4/1991 |
| JP | 04149115 | * | 10/1992 |
| JP | 04149117 | * | 3/1993 |
| WO | 9950258 |   | 7/1999 |

* cited by examiner

*Primary Examiner*—Cephia D. Toomer
(74) *Attorney, Agent, or Firm*—Davidson, Davidson & Kappel, LLC

(57) ABSTRACT

Provided with a novel ascorbic acid derivative represented by the formula (I) and a method for preparing the same:

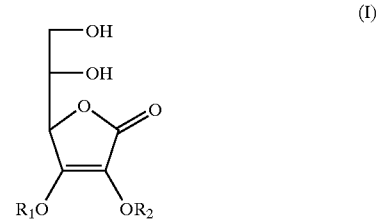

wherein $R_1$ and $R_2$ are different from each other and, independently H or $-CH_2CH_2-(O-CH_2-CH_2)_n-OR_3$, wherein n is an integer from 2 to 400; and $R_3$ is a lower alkyl group having 1 to 10 carbon atoms. The novel ascorbic acid derivatives of this invention have excellent characteristics such as long-lasting anti-oxidation effect, high solubility in both water and organic solvents, and high stability in an aqueous solution. Furthermore, the novel ascorbic acid derivatives are useful for feed, food, cosmetic and pharmaceutical products due to their low toxicity and high thermal stability.

18 Claims, No Drawings

POLYETHOXYLATED ASCORBIC ACID DERIVATIVES AS A NOVEL ANTIOXIDANT AND PROCESS FOR PREPARING THEREOF

This application is a Continuation of PCT International Application Number; PCT/KR99/00148 filed Mar. 27, 1999.

TECHNICAL FIELD

The present invention relates to novel ascorbic acid derivatives and their synthetic method represented by the following general formula (I).

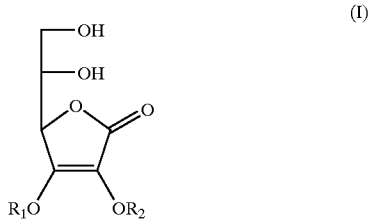

wherein $R_1$ and $R_2$ are different from each other and independently H or —$CH_2CH_2$—(O—$CH_2$—$CH_2$)$_n$—$OR_3$, wherein n is an integer from 2 to 400; and $R_3$ is a lower alkyl group having 1 to 10 carbon atoms.

BACKGROUND ART

L-ascorbic acid is one of the most potent compounds causing as an antioxidant in biological systems by scavenging active oxygen species and free radicals.

L-ascorbic acid is a well-known water-soluble antioxidant that has a whitening effect and serves as a cofactor of prolinehydroxylase to promote synthesis of collagen (see. Quaglino, D. Jr., et al., *J. Biol. Chem,* p272–345, 1997).

L-ascorbic acid is also used in various products requiring a long-term antioxidation effect. But, its usefulness for such products is not so reliable because it is susceptible to heat, light and air.

As such, many studies have been made on the development of ascorbic acid derivatives with enhanced stability while maintaining the antioxidation activity. Notably, a common way to improve the stability of L-ascorbic acid is converting a 2 - or 3-hydroxyl group of L-ascorbic acid to another substituent (see. U.S. Pat. Nos. 5,143,648; 4,780, 549; and 4,177,445, Japanese Patent Sho 52-18191, and Korean Patent No. 91-8733).

L-ascorbic acid, which is a water-soluble antioxidant, is almost insoluble in oil and fat (e.g., salad oil and lard oil). Thus, there is a need of developing ascorbic acid derivatives that have a relatively high solubility in both water and organic solvents, for various use as an antioxidant in foods and cosmetics.

Examples of commercially available derivatives of vitamin C include L-ascorbic acid-6-palmitate, 2,6-dipalmitate, 6-stearate, L-ascorbic acid-3-O-ethyl and magnesium L-ascorbic acid-2-phosphate (see. Korean Patent No. 91-8733, and U.S. Pat. Nos. 5,143,648; and 7,179,445).

Among these compounds, relatively fat-soluble derivatives of ascorbic acid are L-ascorbic acid-6-palmitate, 2,6-dipalmitate and 6-stearate. Despite the improved chemical stability, these derivatives still have a limitation in lasting their anti-oxidative activity because of their rapid decomposition in vitro.

In an attempt to overcome these problems, the inventors of this invention derive novel ascorbic acid derivatives having considerably high solubilities in both water and organic solvents due to a polyethylene glycol moiety introduced at the 2 - or 3-hydroxyl group of L-ascorbic acid. The invention also includes a novel ascorbic acid derivative having high stability and long-lasting anti-oxidation effect.

DISCLOSURE OF INVENTION

The present invention relates to a new stable ascorbic acid.

It is therefore an object of the present invention is to provide a novel ascorbic acid derivative that overcomes the drawbacks of the related art methods.

The invention has solved the problems by introducing a polyethylene glycol moiety at the 2 - or 3-hydroxyl group of L-ascorbic acid. The invention is also directed to an ascorbic acid derivative having a high solubility in both water and most organic solvents and an inhibitory activity against tyrosinase.

It is another object of the present invention to provide a method for preparing such an ascorbic acid derivatives.

To achieve the above object, there is provided a novel ascorbic acid derivative by the formula (I) and a method for preparing the same:

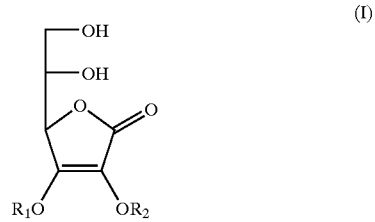

wherein $R_1$ and $R_2$ are independently H or —$CH_2CH_2$—(O—$CH_2$—$CH_2$)$_n$—$OR_3$, wherein n is an integer from 2 to 400; and $R_3$ is a lower alkyl group having 1 to 10 carbon atoms.

There is also provided a method for preparing an ascorbic acid derivative represented by the formula (I), wherein $R_1$ represents —$CH_2CH_2$—(O—$CH_2$—$CH_2$)$_n$—$OR_3$, wherein n and $R_3$ are defined as above. The method includes: (i) reacting cesium ascorbate represented by the formula (V) with a derivative of polyethylene glycol represented by the formula (IV) in an appropriate solvent,

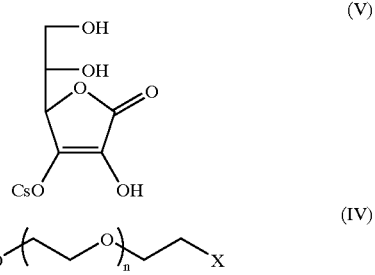

wherein $R_3$ is a lower alkyl group having 1 to 10 carbon atoms; n is an integer from 2 to 400; and X is a halogen atom such Cl, Br and I, or sulfonate such as tosylate, triflate or tresylate.

There is also provided a method for preparing a ascorbic acid derivative represented by the formula (I), wherein $R_1$ is a hydrogen atom and $R_2$ represents —$CH_2CH_2$—(O—$CH_2$—$CH_2$)$_n$$OR_3$, wherein n and $R_3$ are defined as above. More specifically, according to Scheme 1, the method includes: (i) reacting the compound of the formula (V) with benzyl bromide in the presence of a solvent to form 3-O- benzyl ascorbic acid represented by the formula (VI); (ii) reacting 3-O-benzyl ascorbic acid of the formula (VI) with PEG-I in the presence of cesium carbonate in a solvent to form 3-O-benzyl-2-polyethyleneglycolyl-ascorbic acid represented by the formula (VII); and (iii) hydrogenating the compound of the formula (VII) in the presence of a catalyst.

[Scheme I]

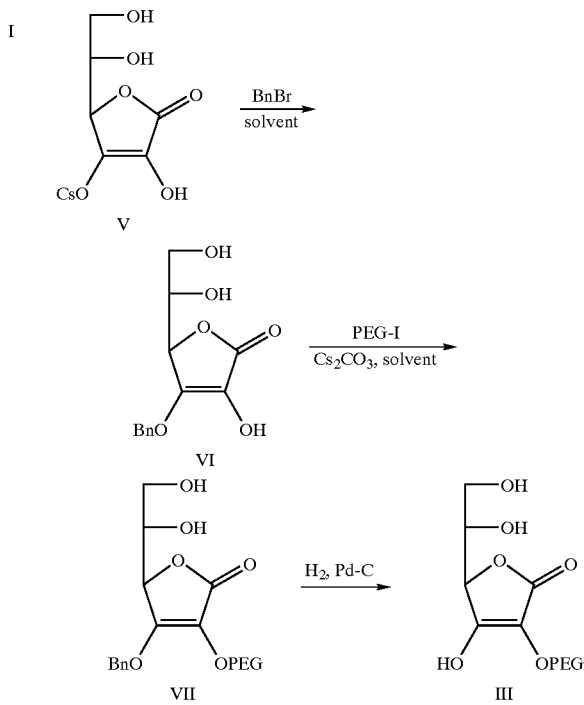

wherein Bn is benzyl group; and PEG is $CH_2CH_2—(O—CH_2—CH_2)_n—OR_3$, wherein n and $R_3$ are defined as above.

Furthermore, a method for preparing a compound of the formula (I) includes: (i) reacting a compound represented by the formula (VIII) with a derivative of polyethylene glycol represented by the formula (IV) in the presence of a base in a solvent; and (ii) hydrolyzing the product in the presence of an acid catalyst,

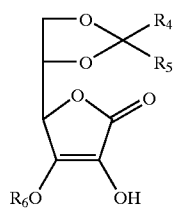

(VIII)

wherein $R_4$ and $R_5$ are the same or different and independently hydrogen atom, methyl group, ethyl group, or $—(CH_2)_m$— bonded to $R_4$ and $R_5$, wherein m is 4 or 5; and $R_6$ is hydrogen atom, benzyl group or paramethoxybenzyl group.

BEST MODE FOR CARRYING OUT THE INVENTION

Hereinafter, the present invention will be described in further detail.

The invention relates to an ascorbic acid derivative which stability is improved by introducing of polyethylene glycol group at the 2 - or 3-hydroxyl group of ascorbic acid.

The novel ascorbic acid derivative can be prepared by two methods: (1) the one method involves preparing a 5,6-O-acetal or ketal of ascorbic acid, introducing a polyethylene glycol group at the 3-OH position of the protected ascorbic acid in the presence of a base, and then eliminating the acetal or ketal group; and (2) the other method involves direct coupling of non-protected ascorbic acid with a polyethoxylated intermediate.

In the first method, in which the final product is obtained from non-protected ascorbic acid, cesium ascorbate represented by the formula (V) reacts with a derivative of polyethylene glycol represented by the formula (IV) in a suitable solvent to produce the compound represented by the formula (II).

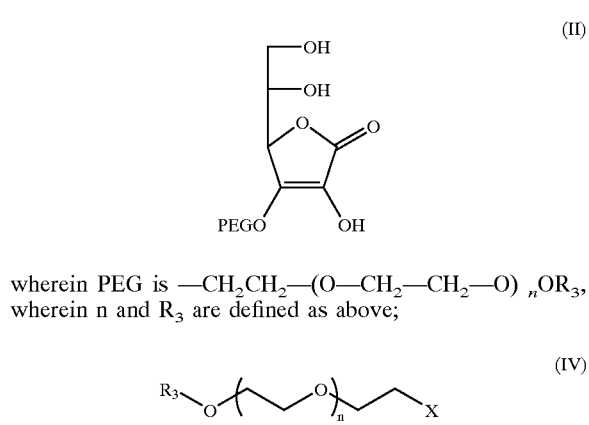

wherein PEG is $—CH_2CH_2—(O—CH_2—CH_2—O)_nOR_3$, wherein n and $R_3$ are defined as above;

wherein $R_3$ is a lower alkyl group having 1 to 10 carbon atoms; n is an integer from 2 to 400; and X is a halogen atom (e.g., Cl, Br or I) or sulfonate (e.g., tosylate, triflate or tresylate).

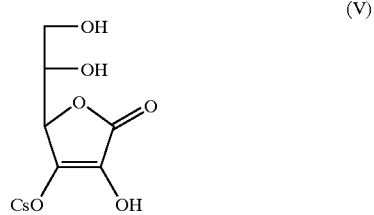

The compound represented by the formula (IV) is denoted by $PEG_n$—X.

The solvent used in this reaction is selected from the group consisting of dimethylsulfoxide (DMSO), dimethylformamide (DMF), hexamethyl phosphoramide (HMPA), N-methylpyrrolidone, pyrrolidone, dimethylacetamide (DMAC), 1,3-dimetyl-3,4,5,6-tetrahydro-2(1H)-pyrimidinone (DMPU), and mixtures thereof.

The compound of the formula (V) as used herein is prepared by reacting ascorbic acid with cesium carbonate in water as a solvent and crystallzing the crude cesium ascorbate in isopropyl alcohol.

In the second method, the final product is obtained from non-protected ascorbic acid, the compound represented by the formula (V) reacts with benzyl bromide in a solvent to give 3-O-benzyl ascorbic acid represented by the formula (VI) and then the compound of formula (VI) is coupled with PEG-I in the presence of cesium carbonate, followed by catalytic hydrogenation, to give a compound represented by the formula (III).

The solvent used in the above reaction is selected from the group consisting of dimethylsulfoxide (DMSO), dimethylformamide (DMF), hexamethyl phosphoramide (HMPA), N-methylpyrrolidone, pyrrolidone, dimethylacetamide (DMAC), 1,3-dimetyl-3,4,5,6-tetrahydro-2(1H)-pyrimidinone (DMPU), and mixtures thereof.

Another method for preparing a compound represented by the formula (I) involves synthesizing a 5,6-O-acetal or ketal of ascorbic acid, introducing a PEG group at the 3-hydroxyl position of ascorbic acid and eliminating the acetal or ketal group. More particularly, an ascorbic acid derivative represented by the formula (II) is prepared as follows.

First, a 5,6-O-acetal or ketal ascorbic acid derivative represented by the formula (IX) reacts with a derivative of polyethylene glycol represented by the formula (IV) in the presence of a base in a suitable solvent to produce a compound represented by the formula (X).

Subsequently, an acetal or ketal group of the compound of the formula (X), is eliminated in the presence of an acid catalyst to obtain an ascorbic acid derivative represented by the formula (II):

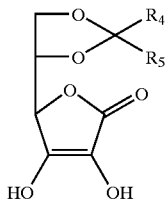

(IX)

wherein $R_4$ and $R_5$ are defined as above; and

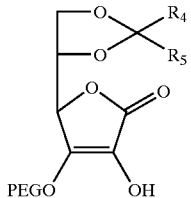

(X)

wherein $R_4$, $R_5$ and PEG are defined as above.

Preferably, a derivative of polyethylene glycol represented by the formula (IV) has a molecular weight of from 50 to 20000, more preferably, 300 to 1000. Examples of the alkyl group denoted by $R_3$ in the formula (IX) include methyl, ethyl, n-propyl, isopropyl, n-butyl, isobutyl, sec-butyl, t-butyl, n-methyl, n-hexyl, n-heptyl, n-octyl, n-nonyl and n-desyl. Examples of the said halogen atom include chlorine, bromine and iodine, and examples of sulfonate include tosylate, triflate and tresylate.

To prepare the compound of the formula (X), the 5,6-O-acetal or ketal ascorbic acid derivative represented by the formula (IX) is subjected to coupling reaction with the compound of the formula (IV) in the presence of a suitable base. Examples of the said base include sodium hydroxide, potassium hydroxide, sodium carbonate, potassium carbonate, cesiun carbonate and sodium hydride. Examples of the suitable solvent include dimethylformamide, dimethylsulfoxide, hexamethyl phosphoramide, N-methylpyrrolidone, pyrrolidone and dimethylacetamide. Preferably, the reaction temperature is from 10 to 90° C. and the reaction time is from 1 to 24 hours.

The compound of the formula (X), obtained from O-alkylation at 3-position of the 5,6-acetal or ketal ascorbic acid derivative, is hydrolyzed to eliminate an acetal or ketal group present at hydroxyl groups at 5 - and 6-positions of ascorbic acid, followed by appropriate isolation and purification. The resulting compound is polyethoxylated ascorbic acid represented by the formula (II).

The above hydrolysis reaction is performed in the presence of an acid catalyst, the examples of the said catalyst include hydrochloric acid, sulfuric acid, p-toluenesulfonic acid, camphorsulfonic acid and acetic acid. Examples of the solvent include methanol, ethanol, methylene chloride, 1,2-methoxyethane and tetrahydrofuran. Preferably, the reaction temperature is from 0 to 70° C. and the reaction time is from 1 to 12 hours.

Alternatively, a ascorbic acid derivative represented by the formula (III) can be prepared by synthesizing 5,6-O-acetal or ketal of ascorbic acid, introducing PEG group at the 3-hydroxyl position of ascorbic acid, and eliminating the acetal or ketal. This method is analogous to the above-stated preparing method for an ascorbic acid derivative represented by the formula (II). More specifically, the compound of the formula (XI) reacts with a derivative of polyethylene glycol represented by the formula (IV) in the presence of a base to produce a compound of the formula (XII), followed by catalytic hydrogenation, to give a compound of the formula (XIII). This compound is then hydrolyzed to produce a compound represented by the formula (III):

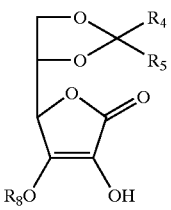

(XI)

wherein $R_4$ and $R_5$ are defined as above; and $R_8$ is benzyl or paramethoxybenzyl group;

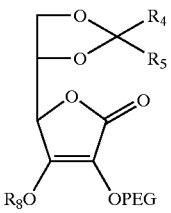

(XII)

wherein $R_4$, $R_5$, $R_8$ and PEG are defined as above.

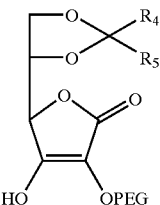

(XIII)

wherein $R_4$, $R_5$, and PEG are defined as above.

The compound of the formula (XI) is obtained by selectively introducing at the 3-hydroxy position of an ascorbic acid with benzyl or paramethoxybenzyl group that can be easily removed through catalytic reduction. To enhance the selectivity of benzylation, the selection of an appropriate solvent and reaction temperature is of importance. Examples of the solvent include dimethylformamide, dimethylsulfoxide, N-methylpyrrolidone, methylethylketone, acetone, methanol and tetrahydrofuran.

Examples of the base used include sodium carbonate, potassium carbonate, cesium carbonate, sodium hydride and potassium t-butylalkoxide. Preferably, the reaction temperature is from 5 to 50° C. and the reaction time is about from 1 to 12 hours.

To prepare a compound of the formula (XII), a compound of the formula (XI) is coupled with a compound of the formula (IV) in the presence of a suitable base. Examples of the said base include sodium hydroxide, potassium hydroxide, sodium carbonate, potassium carbonate, cesium carbonate and sodium hydride.

The resulting compound of the formula (XII) is reduced into a compound represented by the formula (XIII), which is then hydrolyzed to give a compound represented by the formula (III).

The above hydrolysis reaction is performed in the presence of an acid catalyst, the examples of the said catalyst include hydrochloric acid, sulfuric acid, p-toluenesulfonic acid, camphorsulfonic acid and acetic acid. Examples of the solvent used for the hydrolysis include methanol, ethanol, methylene chloride, 1,2-methoxyethane and tetrahydrofuran. Preferably, the reaction temperature is from 0 to 70° C. and the reaction time is from 1 to 12 hours.

The reduction is performed in the presence of a catalyst, e.g., palladium, palladium-carbon, platinum black and platinum oxide in an organic solvent, e.g., methanol, ethanol and ethylacetate.

The present invention will be described below in further detail, which are not intended to limit the present invention.

Preparation Example 1
Synthesis of PEG-I (Formula IV)

$PEG_{550}$-Cl (3.1 g, 5.45 mmol), prepared from the existing literature (Zalipsky, S. et al., *Eur. Polym. J.* 19, 1177, 1983) was dissolved in 5 ml of acetone, followed by the addition of sodium iodide. The reaction mixture was refluxed for 24 hours and cooled to room temperature. After removal of the solvent under reduced pressure, the concentrate was diluted with methylene chloride. The diluted solution was washed with 5% sodium hydrosulfide and the separated aqueous layer was extracted with methylene chloride again. The combined organic layer was dried over sodium sulfate and concentrated under reduced pressure to obtain 3.3 g of $PEG_{550}$-I as an oil phase (yield 95%).

$^1$H-NMR(CDCl$_3$): δ3.76(t, J=6.9 Hz, 2H), 3.67 (bs, —OCH$_2$CH$_2$—), 3.56 (m, 2H), 3.38 (s, 3H), 3.27 (t, J=6.9 Hz, 2H)

Preparation Example 2
Synthesis of Cesium Ascorbate (Formula V)

Ascorbic acid (5 g, 28.4 mmol) was dissolved in 20 ml of water, followed by slow addition of cesium carbonate (4.63 g, 14.2 mmol) in the temperature range of 0 to 5° C. 40 ml of isopropyl alcohol was slowly added to the reaction mixture when the generation of carbon dioxide completely stopped. After standing for several hours, the precipitate was filtered and washed with isopropyl alcohol, and dried to give 8.4 g of the cesium ascorbate as a white solid (yield 95%).

EXAMPLE 1
Synthesis of 3-O-$PEG_{50}$-Ascorbic Acid (Formula II)

Ascorbic acid (560 mg, 3.18 mmol) was dissolved in 4 ml of dimethylsulfoxide, followed by addition of cesium carbonate (518 mg, 1.59 mmol). After 20 minutes, $PEG_{550}$-I (1.94 g, 2.65 mmol, formula (IV)) obtained from Preparation Example 1 was added to the reaction mixture and heated to 60° C. for 18 hours. After removal of dimethylsulfoxide under reduced pressure, the resulting concentrated solution was diluted with methylene chloride and then followed by filtration. The filtrate was concentrated under reduced pressure and purified by column chromatography on silica gel to give 1.23 g of the title compound as a sticky oil (yield 66%).

$^1$H-NMR(CDCl$_3$): δ4.78 (m, 1H), 4.67 (d, J=2.1 Hz, 1H), 4.45 (m, 1H), 4.00 (m, 1H), 3.8–3.5 (bs, —OCH$_2$CH$_2$—), 3.38 (s, 3H)

EXAMPLE 2
Synthesis of 2-O-$PEG_{550}$-Ascorbic Acid (Formula III)

(1) Synthesis of 3-O-benzyl ascorbic acid (Formula VI)

Ascorbic acid (10 g, 56.8 mmol) was dissolved in 60 ml of dimethylsulfoxide, followed by addition of cesium carbonate (9.25 g, 28.4 mmol). After 20 minutes, benzyl bromide (6.75 ml, 56.8 mmol) was added to the reaction mixture and heated to 50° C. for 18 hours. The reaction mixture was cooled down to the room temperature and diluted with 150 ml of dichloromethane to produce a solid. After filtration, the filtrate was concentrated under reduced pressure and purified by column chromatography on silica gel to give 7.2 g of the 3-O-benzyl ascorbic acid (yield 48%).

$^1$H-NMR(CDCl$_3$): δ7.3 (m, 5H), 5.51 (d, J=11.7 Hz, 1H), 5.43 (d, J-11.7 Hz, 1H) 4.64 (d, J=1.8 Hz, 1H), 4.2–3.0 (m, 7H)

(2) Synthesis of 3-O-benzyl-2-$PEG_{550}$-ascorbic acid (Formula VII)

3-O-benzyl-ascorbic acid (0.5 g, 1.88 mmol), obtained from example 2-(1), was dissolved in 4 ml of dimethylsulfoxide, followed by addition of cesium carbonate (3.6 mg, 0.94 mmol). After 20 minutes, $PEG_{550}$-I (1.12 g, 1.7 mmol) was added to the reaction mixture and heated to 60° C. for 1.5 hours. The reaction mixture was cooled down to the room temperature and extracted with methylene chloride. The organic layer was washed with water, dried over sodium sulfate and then concentrated under reduced pressure. The concentrate was purified by column chromatography on silica gel to give 830 mg of the 3-O-benzyl-2-$PEG_{550}$-ascorbic acid as a waxy liquid (yield 61%).

$^1$H-NMR(CDCl$_3$): δ7.4 (m, 5H), 5.62 (d, J=11.7 Hz, 1H), 5.56 (d, J-11.7 Hz, 1H), 4.70 (d, J=2.1 Hz, 1H), 4.40 (m, 1H, 4.20 (m, 1H), 3.98 (m, 1H), 3.8–3.5 (bs, —OCH$_2$CH$_2$—), 3.38 (s, 3H)

(3) Synthesis of 2-O-$PEG_{550}$-ascorbic acid (Formula III)

3-O-benzyl-2-O-$PEG_{550}$-ascorbic acid (4.04 g, 5 mmol), obtained from example 2-(2), was dissolved in 40 ml of methanol, followed by addition of 10% Pd-C 400 mg. The reaction mixture was stirred at the room temperature for 2 hours under the hydrogen atmosphere. The reaction mixture was then filtered and washed with methanol. The filtrate was concentrated under reduced pressure to give 3.0 g of the 3-O-benzyl-2-$PEG_{550}$-ascorbic acid as a sticky oil (yield 85%).

$^1$H-NMR(CDCl$_3$): δ4.01 (br, J=4.8 Hz, 2H), 3.73 (m, 1H), 3.60 (br, t, 2H), 3.5 (bs, —OCH$_2$CH$_2$—), 3.23 (s, 3H)

EXAMPLE 3
Synthesis of 3-O-$PEG_{350}$-Ascorbic Acid (formula II)

(1) 5,6-O-isopropylidene ascorbic acid (21.62 g, 0.1 mole) was dissolved in 150 ml of dimethylsulfoxide, followed by addition of potassium carbonate (8.29 g, 0.06 mole) and $PEG_{350}$-I (46.0 g, 0.1 mole, Formula IV) at the room temperature. The reaction mixture was stirred at the room temperature for 1 hour and warmed to 50° C. for 4 hours. After cooled to the room temperature, the reaction mixture was diluted with 100 ml of dichlorometane. The diluted solution was washed with 50 ml of 10% aqueous sodium chloride solution three times and then dried over anhydrous magnesium sulfate, followed by filtration. The filtrate was concentrated under reduced pressure and purified on column chromatography ($SiO_2$, 270–400 mesh, dichloromethane:methanol=15:1, v/v), thus obtaining 44.95 g of 5,6-O-isopropylidene-3-O-$PEG_{350}$-ascorbic acid (Formula X) as a sticky oil (yield 82%, purity 98%).

$^1$H-NMR($CDCl_3$): δ4.58 (m, 3H), 4.26 (m, 1H), 4.15 (t, 1H), 4.00 (m, 1H), 3.8–3.5 (bs, —$OCH_2CH_2$—), 3.38 (s, 3H), 1.35 (d, 6H)

(2) 5,6-O-isopropylidene-3-O-$PEG_{350}$-ascorbic acid (Formula X) (44.95 g, 0.082 mole) was dissolved in 140 ml of methanol and the reaction mixture was cooled to 0° C. Then, 105 ml of 2M HCl was slowly added dropwise. The reaction mixture was slowly warmed to 25° C. and stirred at the room temperature for 3 hours. The reaction mixture was then neutralized with sodium bicarbonate and evaporated under reduced pressure to remove water and methanol. The concentrate was purified on column chromatography ($SiO_2$, dichloromethane:methanol=20:1, v/v) to give 37.50 g of 3-O-$PEG_{350}$-ascorbic acid (Formula II) (yield 90%).

$^1$H-NMR($CDCl_3$): δ4.78 (m, 1H), 4.67 (d, 1H), 4.45 (m, 1H), 4.00 (m, 1H), 3.8–3.5 (bs, —$OCH_2CH_2$—), 3.38 (s, 3H)

(3) 5,6-O-isopropylidene ascorbic acid (Formula IX) was prepared according to a known procedure specified in the literature [*J. Med. Chem*, 31, 793, 1988]. More specifically, 8.64 g (0.11 mole) of acetyl chloride was added to the mixture of 88.06 g (0.5 mol) of L-ascorbic acid and acetone (500 g), and the reaction mixture was vigorously stirred at the room temperature for 12 hours, followed by filtration. The filter cake was washed with cold acetone and dried to obtain 84.51 g of 5,6-O-isopropylidene ascorbic acid as a while solid (yield: 78.2%).

(4) $PEG_{350}$-I (Formula IV) was prepared from polyethylene glycol monomethyl ether according to the following two-step synthesis: (i) polyethylene glycol monomethyl ether (350.0 g, 1.0 mole) was dissolved in 1 liter of toluene and dried by azeotropic distillation. 303.57 g (3.0 mole) of triethylamine was added to the solution and then 228.78 g (1.2 mole) of p-toluene sulfonyl chloride was slowly added at 10° C. The reaction mixture was stirred for 1 hour at 10° C. and further 3.5 hours at 25° C., followed by filtration. The filtrate was distilled under reduced pressure and diluted with 400 ml of water. The aqueous solution was extracted with 500 ml of n-hexane and further 1 liter of dichloromethane. The organic layer was dried over anhydrous magnesium sulfate, filtered and distilled under reduced pressure to obtain 494.10 g of $PEG_{350}$OTs as a colorless liquid (yield 98%); and (ii) the resultant $PEG_{350}$OTs (494.10 g, 0.98 mole) was dissolved in 850 ml of acetone and 218.87 g (1.47 mole) of sodium iodide was slowly added to the solution at the room temperature. The reaction mixture was heated to 50° C. and stirred for 8 to complete the reaction. The reaction mixture was cooled, filtered and distilled under reduced pressure. The residue was dissolved in dichloromethane and washed with water. The organic layer was dried over anhydrous magnesium sulfate, filtered and distilled under reduced pressure to obtain 432.72 g of $PEG_{350}$I (yield 96.0%).

$^1$H-NMR($CDCl_3$): δ3.8–3.5 (bs, —$OCH_2CH_2$—), 3.38 (s, 3H), 3.24 (t, 2H)

EXAMPLE 4

Synthesis of 2-O-$PEG_{350}$-Ascorbic Acid (Formula III)

(1) 30.63 g (0.1 mole) of 5,6-O-isopropylidene-3-O-benzyl ascorbic acid (Formula XI) was dissolved in 150 ml of dimethylsulfoxide and 8.29 g (0.06 mole) of potassium carbonate was added to the solution. The reaction mixture was stirred for 30 minutes, followed by adding 46.0 g (0.1 mole) of $PEG_{350}$-I. The reaction mixture was heated to 50° C. for 2 hours, cooled to the room temperature and diluted with 100 ml of dichloromethane. The diluted mixture was then washed with 50 ml of 10% aqueous sodium chloride solution three times. The organic layer was dried over anhydrous magnesium sulfate and filtered. The filtrate was distilled under reduced pressure and purified on column chromatography ($SiO_2$, dichloromethane:methanol=10:1, v/v) to give 54.9 g of 5,6-O-isopropylidene-3-O-benzyl-2-O-$PEG_{350}$ ascorbic acid an oily product (Formula XII) (yield 86.0%).

(2) 54.9 g (0.08 mole) of 5,6-O-isopropylidene-3-O-benzyl-2-O-$PEG_{350}$ ascorbic acid (Formula XII) was dissolved in 80 ml of methanol and 10% pd-C (1.37 g) was added to the solution. The reaction mixture was stirred for 2 hours under hydrogen atmosphere and the catalyst was filtered out. The filtrate was concentrated under reduced pressure to give 43.14 g of 5,6-O-isopropylidene-2-O-$PEG_{350}$ ascorbic acid (Formula XIII) (yield 91.5%).

(3) 43.14 g (0.079 mole) of 5,6-O-isopropylidene-2-O-$PEG_{350}$ ascorbic acid (Formula XIII) was dissolved in 140 ml of methanol, and 114 ml of 2M HCl was added to the solution at 0° C. The reaction mixture was heated to 25° C. and stirred for 3 hours. The reaction mixture was neutralized with sodium bicarbonate and evaporated to remove water and ethanol under reduced pressure. The concentrated filtrate was purified on column chromatography ($SiO_2$, dichloromethane:methanol=20:1, v/v) to give 36.33 g of 2-O-$PEG_{350}$ ascorbic acid (Formula III) (yield 90.5%).

$^1$H-NMR($CDCl_3$): δ4.0 (m, 2H), 3.73 (m, 1H), 3.60 (m, 2H), 3.5 (bs, —$OCH_2CH_2$—), 3.23 (s, 3H)

(4) 5,6-O-isopropylidene-3-O-benzyl ascorbic acid (Formula XI) was prepared according to a known procedure specified in the literature (*Terahedron*, 52, 1293, 1996).

Experimental Example 1

Inhibitory Activity Against Tyrosinase

Tyrosinase extracted from mushrooms was purchases from Sigma Co. First, L-tyrosine as a substrate was dissolved in a 0.05M phosphate buffer solution (pH 6.8) to have a concentration of 1.5 mM. 0.01 ml of this solution was added to a 0.3 ml spectrophotometer cuvette, followed by 0.01 ml of 0.06 mM dihydroxyphenylalamine (DOPA) as a cofactor. To this solution were added compounds of Formulas (II) and (III) and the phosphate buffer solution to have the total volume of 0.1 ml. Then, 0.1 ml of enzyme solution containing 60 U/ml of tyrosinase in the phosphate buffer solution was added to the substrate solution. Meanwhile, a blank was prepared by adding only 0.1 ml of the phosphate buffer solution. The reaction was performed at 37° C. for 10 minutes. The absorbance was measured at 475 nm with a spectrophotometer (Beckman DU-7500) to determine the inhibitory rate against tyrosinase. $IC_{50}$ value was determined as the concentration of the inhibitor whose inhibitory rate against the enzyme amounts to 50%. The inhibitory rate is calculated according to the following equation and the results are presented in Table 1.

Inhibitory Rate(%)=[(A−B)/A]×100 wherein A is the absorbance at 475 nm in a solution containing no inhibitor, and B is the absorbance at 475 nm in a solution containing an inhibitor.

TABLE 1

Tyrosinase Inhibitory Activity ($IC_{50}$)

| Compound | $IC_{50}$ ($\times 10^{-3}$M) |
| --- | --- |
| 3-O-PEG$_{350}$-ascorbic acid | 9.80 |
| 3-O-PEG$_{550}$-ascorbic acid | 7.06 |
| 2-O-PEG$_{350}$-ascorbic acid | 1.97 |
| 2-O-PEG$_{550}$-ascorbic acid | 7.06 |
| 3-O-Ethyl-ascorbic acid | 9.80 |
| Ascorbic acid | 0.47 |

Experimental Example 2
Radical Scavenging Effect

The compounds prepared according to examples 1 to 4 were analyzed in regard to radical scavenging effect as follows.

Measurement was made using the 1,1-diphenyl-2-picrylhydrazyl (DPPH) method [Blois, M. S. Nature, 1958, 181, 1190]. DPPH is a relatively stable radical with the maximum absorption at 517 nm. The absorption at this wavelength disappears upon removal of the radical. DPPH was purchased from Sigma Co. and dissolved in methanol to make the concentration of 0.5 mM.

First, 100 μl of each solution ($10^{-1}$ to $10^{-6}$ M) of the individual compounds prepared in examples 1 to 4 were placed in each well of a 96-well plate. After adding 100 μl of DPPH solution and standing the reaction mixture at the room temperature, the absorption at 517 nm was measured for each well using a micro plate reader (BioTeck EL-340). A blank solution was prepared to contain 100 μl of methanol instead of the above compounds. The concentration of the individual compounds was denoted by $IC_{50}$ at the time when the absorption of the test sample becomes a half of that of the blank solution. The absorption was measured at 1 hour and at 24 hours after treatment. The results are presented in Table 2.

TABLE 2

Radical Scavenging Effect

| | $IC_{50}$ ($\times 10^{-3}$M) | |
| --- | --- | --- |
| Compound | After 1 hour | After 24 hrs. |
| 3-O-PEG$_{350}$-ascorbic acid | 78.7 | 5.9 |
| 3-O-PEG$_{550}$-ascorbic acid | 423.6 | 112.9 |
| 2-O-PEG$_{350}$-ascorbic acid | 7.9 | 5.9 |
| 2-O-PEG$_{550}$-ascorbic acid | 7.9 | 4.2 |
| 3-O-Ethyl-ascorbic acid | 9.8 | 9.8 |
| Ascorbic acid | 3.4 | 3.4 |

As shown in Table 2, the novel ascorbic acid derivatives of this invention were slightly inferior in the radical scavenging effect to a free ascorbic acid, which 2-OH and 3-OH group was not substituted, but much superior to a known ascorbic acid derivative, 3-O-ethyl-ascorbic acid. The compounds polyethoxylated at the 2-hydroxyl position of ascorbic acid, such as 2-O-PEG$_{350}$ ascorbic acid and 2-O-PEG$_{550}$ ascorbic acid showed a potent radical scavenging effect in a short time irrespective of their molecular weight. Meanwhile, the compounds polyethoxylated at the 3-hydroxyl position of ascorbic acid, such as 3-O-PEG$_{350}$ ascorbic acid and 3-O-PEG$_{550}$ ascorbic acid had a significant difference in the radical scavenging effect depending on their molecular weight and showed persistency, i.e., an increase in the radical scavenging effect with an elapse of time.

Experimental Example 3
Stability in Aqueous Solution

The compounds prepared in examples 1 to 4 were analyzed in regard to stability in an aqueous solution as follows.

First, 0.1% aqueous solutions of the individual compounds of examples 1 to 4 and ascorbic acid were prepared. After 8 weeks, the changes in the contents of ascorbic acid derivatives depending on pH at 40° C. were measured by HPLC. The results are presented in Table 3 in terms of recovery rate (%)=(assay value after 8 weeks)/(initial assay value)×100.

TABLE 3

Stability in Aqueous Solution

| | Recovery Rate (%) | | | |
| --- | --- | --- | --- | --- |
| Compound | pH 4 | PH 5 | PH 6 | PH 7 |
| 3-O-PEG$_{350}$-ascorbic acid | 91.4 | 89.2 | 85.4 | 63.5 |
| 3-O-PEG$_{550}$-ascorbic acid | 78.5 | 70.8 | 61.3 | 42.5 |
| 2-O-PEG$_{350}$-ascorbic acid | 90.8 | 89.5 | 84.3 | 59.8 |
| 2-O-PEG$_{550}$-ascorbic acid | 91.1 | 89.9 | 85.7 | 62.4 |
| 3-O-Ethyl-ascorbic acid | 91.0 | 89.1 | 86.0 | 65.0 |
| Ascorbic acid | 38.2 | 27.5 | — | — |

As shown in Table 3, the novel ascorbic acid derivatives of this invention had a long-lasting stability in an aqueous solution relative to free ascorbic acid.

Experimental Example 4
Thermal Stability

3-O-PEG$_{350}$-ascorbic acid prepared in example 3 was analyzed in regard to thermal stability in the neat state as follows.

First, 3-O-PEG$_{350}$-ascorbic acid and other ascorbic acid derivatives were placed in an oven at 120° C. and the changes in the contents of ascorbic acid derivatives over time were measured by HPLC. The results are presented in Table 4 in terms of recovery rate (%)=(assay value over time)/(initial assay value)×100.

TABLE 4

Thermal Stability

| | Recovery Rate (%) | | | | | |
| --- | --- | --- | --- | --- | --- | --- |
| Compound | 0 hr | 1.5 hr | 4.0 hrs | 24.0 hrs | 48.0 hrs | 120 hrs |
| 3-O-PEG$_{350}$-ascorbic acid | 98.4 | 98.3 | 97.5 | 95.2 | 92.3 | 90.9 |
| Ascorbic acid | 99.2 | 95.3 | 85.0 | 75.0 | 56.0 | 46.0 |
| 2-O-ethyl-ascorbic acid | 98.7 | 87.1 | 79.3 | 76.1 | 68.5 | 61.3 |
| Ascorbic-2-polyphosphate | 98.1 | 84.1 | 76.5 | 70.4 | 63.2 | 57.5 |
| phosphate | 98.1 | | | | | |

Experimental Example 5
Transdermal Absorption Test

3-O-PEG$_{350}$-ascorbic acid prepared in example 3 was subjected to the transdermal absorption test using $H_2O$ as a carrier vehicle.

More specifically, a dorsal skin of 8-weeks aged female mouse (naked mouse) was cut off and then 5% (w/v) solution of the test sample was applied in an amount of 50 μl to the skin having a size of 1.7 cm². Using the apparatus for measuring transdermal absorption test (Franz cell), after 24 hours, the absorbed material was extracted from 7 ml of the receptor solution [50 mM PBS buffer solution (pH=7.4) containing 2% Vol PO20 polyethylene oleyl ether (HLB=16)] and then quantitatively analyzed by HPLC. The results are presented in Table 5.

TABLE 5

| Compound | Transdermal absorption Unit (mg) | |
|---|---|---|
| | Total Transdermal Absorption Amount | Absorption Rate (%) |
| Ascorbic acid | 0.03 | 1.2 |
| Ascorbic-2-poly-phosphate | 0.037 | 1.5 |
| 3-O-PEG$_{350}$-ascorbic acid | 0.3 | 12.0 |

As shown in Table 5, the novel ascorbic acid derivative according to example 3 had an eight-fold transdermal absorption rate of that of the related art vitamin C.

Industrial Applicability

As described above in detail, the novel ascorbic acid derivatives of this invention have excellent characteristics such as long-lasting anti-oxidation effect, high solubility in both water and organic solvents, and high stability in an aqueous solution. Furthermore, the novel ascorbic acid derivatives are useful for feed, food, cosmetic and pharmaceutical products due to their low toxicity and high thermal stability.

What is claimed is:

1. A ascorbic acid derivative represented by the following general formula (I):

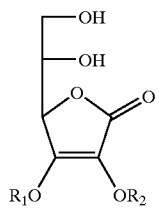

(I)

wherein $R_1$ and $R_2$ are different, and represent a hydrogen atom or —CH$_2$CH$_2$—(O—CH$_2$—CH$_2$)$_n$—OR$_3$ wherein, n is an integer of 2 to 400, $R_3$ is a lower alkyl group of 1 to 10 carbon atoms.

2. The compound of claim 1, wherein said ascorbic acid derivative represented by formula (I) is a compound represented by formula (II):

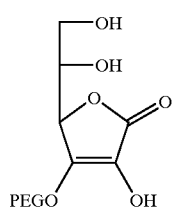

(II)

wherein PEG represents —CH$_2$CH$_2$—(O—CH$_2$—CH$_2$)$_n$—OR$_3$ wherein, n and $R_3$ are defined as in claim 1.

3. The compound of claim 1, wherein said ascorbic acid derivative represented by formula (I) is a compound represented by formula (III):

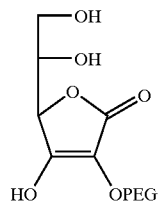

(III)

wherein PEG is —CH$_2$CH$_2$—(O—CH$_2$—CH$_2$)$_n$—OR$_3$, wherein n and $R_3$ are as defined in claim 1.

4. A process for preparing the compound of formula (II) as defined in claim 2 which comprises:
reacting a compound of formula (V):

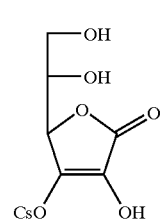

(V)

with a polyethylene glycol derivative of formula (IV) in the presence of a solvent

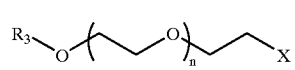

(IV)

wherein $R_3$ is a lower alkyl group of 1 to 10 carbon atoms, n is an integer of 2 to 400, and X represents a halogen atom selected from the group consisting of chlorine, bromine and iodine or a sulfonate selected from the group consisting of tosylate, triflate and tresylate.

5. A process for preparing the compound of formula (II) as defined in claim 2 which comprises:
reacting a compound of formula (IX):

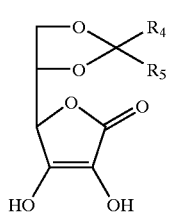

(IX)

wherein $R_4$ and $R_5$ are the same or different, and each represent a hydrogen atom, methyl group or ethyl group, or $R_4$ and $R_5$ are combined to form a cyclic compound of —(CH$_2$)$_m$— wherein, m is 4 or 5 with a polyethylene glycol derivative of formula (IV)

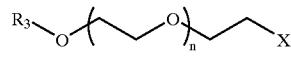

(IV)

wherein $R_3$ is a lower alkyl group of 1 to 10 carbon atoms, n is an integer of 2 to 400, and X is a halogen atom selected from chlorine, bromine or iodine, or a sulfonate selected from tosylate, triflate or tresylate, in the presence of a base and a solvent to give a compound of the formula (X) and then, followed by hydrolysis of a compound of formula (X) with an acid catalyst.

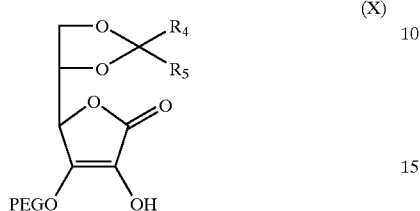

(X)

6. A process for preparing the compound of formula (III) as defined in claim 3 comprising reacting the compound of formula (VI):

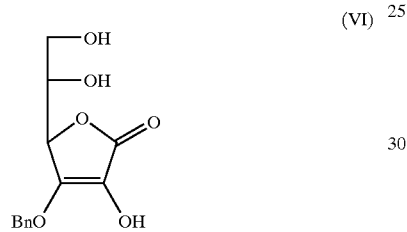

(VI)

with a polyethylene glycol derivative of formula (IV)

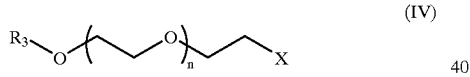

(IV)

wherein Bn is benzyl, $R_3$ is a lower alkyl group of 1 to 10 carbon atoms, n is an integer of 2 to 400, and X is a halogen atom selected from chlorine, bromine or iodine, or a sulfonate selected from tosylate, triflate or tresylate, in the presence of a base and a solvent to give the compound of formula (VII) and then, followed by hydrogenation of the compound of formula (VII) in the presence of a catalyst.

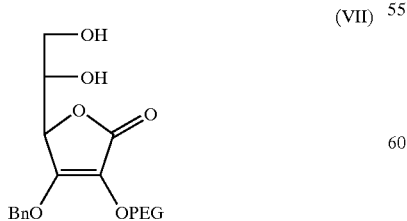

(VII)

7. A process for preparing the compound of formula (III) as defined in claim 3 comprising reacting a compound of formula (XI):

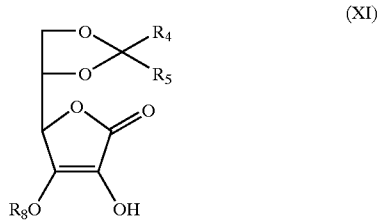

(XI)

wherein $R_4$ and $R_5$ are the same or different and each represent a hydrogen atom, methyl group or ethyl group, or $R_4$ and $R_5$ are combined to form a cyclic compound of —$(CH_2)_m$— wherein m is 4 or 5; $R_8$ is benzyl group or paramethoxybenzyl group, with a polyethylene glycol derivative of formula (IV)

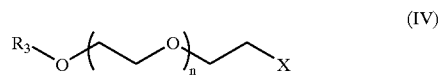

(IV)

wherein $R_3$ is a lower alkyl group of 1 to 10 carbon atoms, n is an integer of 2 to 400, and X is a halogen atom selected from chlorine, bromine or iodine, or a sulfonate selected from tosylate, triflate or tresylate, in the presence of a base and a solvent to give a compound of the following formula (XII)

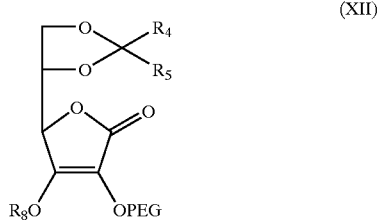

(XII)

wherein $R_4$, $R_5$ and $R_8$ are defined as above, followed by hydrogenation of a compound of formula (XII) in the presence of catalyst to obtain a compound of the following formula (XIII)

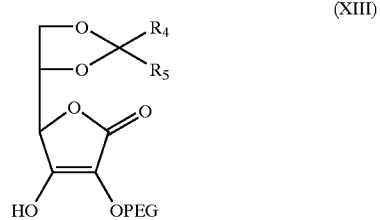

(XIII)

wherein $R_4$ and $R_5$ are defined above, and then followed by hydrolysis of a compound of formula (XIII) with an acid catalyst.

8. The process according to claim 4, wherein the solvent is one or more selected from the group consisting of dimethylsulfoxide, dimethylformamide, hexamethyl phosphoramide, N-methylpyrrolidone, pyrrolidone, dimethylacetamide and 1,3-dimethyl-3,4,5,6-tetrahydro-2(1H)-pyrimidinone.

9. The process according to claim 5, wherein the acid catalyst is selected from the group consisting of hydrochloric acid, sulfuric acid, p-toluenesulfonic acid, camphorsulfonic acid and acetic acid.

10. The process according to claim 5, wherein the base is one or more selected from the group consisting of sodium hydroxide, potassium hydroxide, sodium carbonate, potassium carbonate, cesium carbonate and sodium hydride.

11. The process according to claim 6, wherein the hydrogenation catalyst is selected from the group consisting of palladium, palladium-carbon, platinum black and platinum dioxide.

12. The process according to claim 5, wherein the solvent is one or more selected from the group consisting of dimethylsulfoxide, dimethylformamide, hexamethyl phosphoramide, N-methylpyrrolidone, pyrrolidone, dimethylacetamide and 1,3-dimethyl-3,4,5,6-tetrahydro-2(1H)-pyrimidinone.

13. The process according to claim 6, wherein the solvent is one or more selected from the group consisting of dimethylsulfoxide, dimethylformamide, hexamethyl phosphoramide, N-methylpyrrolidone, pyrrolidone, dimethylacetamide and 1,3-dimethyl-3,4,5,6-tetrahydro-2(1H)-pyrimidinone.

14. The process according to claim 7, wherein the solvent is one or more selected from the group consisting of dimethylsulfoxide, dimethylformamide, hexamethyl phosphoramide, N-methylpyrrolidone, pyrrolidone, dimethylacetamide and 1,3-dimethyl-3,4,5,6-tetrahydro-2(1H)-pyrimidinone.

15. The process according to claim 7, wherein the acid catalyst is selected from the group consisting of hydrochloric acid, sulfuric acid, p-toluenesulfonic acid, camphorsulfonic acid and acetic acid.

16. The process according to claim 6, wherein the base is one or more selected from the group consisting of sodium hydroxide, potassium hydroxide, sodium carbonate, potassium carbonate, cesium carbonate and sodium hydride.

17. The process according to claim 7, wherein the base is one or more selected from the group consisting of sodium hydroxide, potassium hydroxide, sodium carbonate, potassium carbonate, cesium carbonate and sodium hydride.

18. The process according to claim 7, wherein the hydrogenation catalyst is selected from the group consisting of palladium, palladium-carbon, platinum black and platinum dioxide.

* * * * *